United States Patent
Kobayashi et al.

(10) Patent No.: US 6,622,095 B2
(45) Date of Patent: Sep. 16, 2003

(54) APPARATUS FOR DETERMINING CONCENTRATIONS OF HEMOGLOBINS

(75) Inventors: Naoki Kobayashi, Tokyo (JP); Takashi Usuda, Tokyo (JP); Michio Kanemoto, Tokyo (JP); Yoshiaki Takamura, Tokyo (JP); Teiji Ukawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 23 days.

(21) Appl. No.: 10/075,623

(22) Filed: Feb. 15, 2002

(65) Prior Publication Data

US 2002/0111748 A1 Aug. 15, 2002

Related U.S. Application Data

(63) Continuation-in-part of application No. 09/725,865, filed on Nov. 30, 2000, now Pat. No. 6,415,236.

(30) Foreign Application Priority Data

Nov. 30, 1999 (JP) ............................................ 11-339605
Sep. 21, 2000 (JP) ...................................... 2000-286927
Feb. 15, 2001 (JP) ......................................... 2001-38490

(51) Int. Cl.[7] ........................... A61B 5/00; G06F 159/00
(52) U.S. Cl. ............................ 702/31; 702/30; 702/19; 600/322
(58) Field of Search .............................. 702/31, 30, 19; 600/322, 323, 326; 356/39, 40, 41

(56) References Cited

U.S. PATENT DOCUMENTS 5,385,143 A * 1/1995 Aoyagi ........................ 600/310
5,413,100 A 5/1995 Barthelemy et al.
5,503,148 A 4/1996 Pologe et al.
5,720,284 A 2/1998 Aoyagi et al.
5,830,137 A 11/1998 Scharf
5,842,979 A 12/1998 Jarman
5,983,122 A 11/1999 Jarman et al.
6,415,236 B2 * 7/2002 Kobayashi et al. ........... 702/30
6,438,396 B1 * 8/2002 Cook et al. .................. 600/310

FOREIGN PATENT DOCUMENTS

| JP | 53-26437 | 8/1978 |
| JP | 5-228129 | 9/1993 |
| JP | 5-88609 | 12/1993 |
| JP | 8-322822 | 12/1996 |

* cited by examiner

Primary Examiner—Kamini Shah
(74) Attorney, Agent, or Firm—Sughrue Mion, PLLC

(57) ABSTRACT

An apparatus for determining concentrations of hemoglobins includes a light source for emitting lights of at least three different wavelengths, a first wavelength in a near-infrared region, a second wavelength in a red region, and a third wavelength in a red orange region, light receiving device for receiving light emitted by the light source, transmitted through a living tissue or reflected by the living tissue, attenuation ratio processing device for processing attenuation ratios between the wavelengths in accordance with variations of received-light output signals in each of the wavelengths output from the light receiving device, the variations are caused by a pulsation of blood and concentration ratio processing device for processing concentration ratios of at least oxyhemoglobin and methemoglobin based on the output signals from the attenuation ratio processing device.

19 Claims, 9 Drawing Sheets

APPARATUS FOR DETERMINING CONCENTRATIONS OF HEMOGLOBINS

CROSS-REFERENCE TO RELATED APPLICATIONS

This is a continuation-in-part of U.S. patent application Ser. No. 09/725,865 filed Nov. 30, 2000, now U.S. Pat. No. 6,415,236 the entire contents of which are hereby incorporated by reference in this application.

STATEMENT REGARDING FEDERALLY SPONSORED RESEARCH OR DEVELOPMENT (NOT APPLICABLE)

BACKGROUND OF INVENTION

1. Field of the Invention

The present invention relates to measurements of oxygen saturation and concentrations of hemoglobins in arterial blood by using a pulse oximeter, and more particularly to measurement of a concentration of methemoglobin (MetHb).

2. Related Art

A conventional pulse oximeter is constructed such that near-infrared rays of light and red rays of light are irradiated onto a living tissue, ratios of the pulsating components of attenuations of these lights having passed through the living tissue are processed, and an arterial oxygen saturation is noninvasively measured from the result of the processing.

The measuring principle of the pulse oxometer is known as disclosed in JP-A-53-26437, proposed by the applicant of the present patent application. The measuring principle of the pulse oximeter will be described in brief hereunder.

For example, suppose a living tissue R is divided into a blood layer R1 and a layer R2 of a tissue other than blood this tissue will be referred to as a pure tissue), and it is assumed that a thickness of the blood layer R1 is pulsated, but a thickness of the pure tissue layer R2 is not pulsated, viz., it is constant. Where the living tissue R is irradiated with light, an incident light amount IO is reduced by the living tissue R, and an amount of light passing through the living tissue R is I. when a thickness of the blood layer R1 is pulsated to be increased by $\Delta Db$, the amount of the transmitted light is reduced to be $(I-\Delta I)$. In this case, an attenuation $\Delta A$ of the light, which is produced by a thickness change $\Delta Db$ of the blood layer R1, is given by $$\Delta A = \log[I/(I-\Delta I)]$$

When lights of different wavelengths $\lambda 1$ and $\lambda 2$ are irradiated onto the living tissue R, a ratio $\Phi$ of attenuations $\Delta A1$ and $\Delta A2$ of lights of the wavelengths $\lambda 1$ and $\lambda 2$, which are produced by the pulsation of the tissue thickness is mathematically approximated by $$\Phi = \Delta A1/\Delta A2 = \sqrt{\{E1(E1+F1)\}}/\sqrt{\{E2(E2+F2)\}} \quad (1)$$

This is theoretically and empirically confirmed.

In the above expression, Ei is an absorption coefficient of hemoglobin, Fi is a scattering coefficient of light in blood, and i=1, 2, which represent the wavelengths $\lambda 1$ and $\lambda 2$. Assuming that light absorbing materials in blood are only oxyhemoglobin and deoxyhemoglobin, then the absorption coefficient Ei of the hemoglobin is given by the following expression.

$$Ei = SEoi + (1-S)Eri \quad (2)$$

In the expression, S is an oxygen saturation, and Eoi is an absorption coefficient of oxyhemoglobin and Eri is an absorption coefficient of deoxyhemoglobin. Substituting the expression (2) for the expression (1), then we have the following expression $$\Phi = \Delta A1/\Delta A2 = \sqrt{[\{SEo1+(1-S)Er1\}[\{SEo1+(1-S)Er1\}+F1]]}/\sqrt{[\{SEo2+(1-S)Er2\}[\{SEo2+(1-S)Er2\}+F2]]} \quad (3)$$

In the expression (3), Eo1, Er1, Eo2, Er2 F1 and F2 are known values. Therefore, an oxygen saturation S can be obtained in a manner that $\Phi = \Delta A1/\Delta A2$ is measured, substituted for the expression (3), and the expression is solved for the S.

If methemoglobin MetHb is present in blood, a drop arises in a reading of a degree of oxygen saturation measured by a related-art pulse oximeter using two wavelengths; that is, near-infrared rays of light and red rays of light. Since the oximeter cannot determine a concentration of methemoglobin MetHb, the presence/absence or concentration of methemoglobin MetHb in blood (also called a "blood methemoglobin MetHb concentration") remains uncertain until blood of interest is sampled and subjected to measurement performed by a carbon monoxide oximeter (CO-Oximeter).

Meanwhile, where the arterial blood pulsates, the theory teaches that concentration ratios of "n" number of light absorbing materials in the blood can be measured by using "n" number of wavelengths of lights. Accordingly, the theory also teaches that it is impossible to measure concentration ratios of three hemoglobins, oxyhemoglobin O2Hb, deoxyheoglobin RHband methemoglobin MetHb by using two wavelengths of lights, and at least three wavelengths must be used for the measurement.

Actually, however, the influence by pure tissues other than the blood will produce measuring errors. Accordingly, to accurately measure concentrations of "n" number of light absorbing materials in the blood, it is preferable to use (n+1) number of wavelengths, this fact was found and confirmed by us. The applicant of the present patent application developed an apparatus for determining concentrations of materials in blood based on the above fact, and filed the patent application on the apparatus (JP-B-5-88609). Other light absorbing materials, such as carboxyhemoglobin (COHb) and bilirubin, are also contained in the blood. To remove the influence by those materials is attempted, the number of wavelengths used is further increased, and further cost to manufacture the apparatus is also increased.

In adding a third wavelength for measuring the methemoglobin Metub to the pulse oximeter (JP-A-5-228129), the ratio of absorption coefficients of oxyhemoglobin $O_2Hb$ and methemoglobin MetHb at the wavelengths of lights, which are longer than the red wavelengths, as shown in FIG. 11, is almost constant. For this reason, where the third wavelength is selected from those wavelengths longer than the red wavelengths it is very difficult to determine the methemoglobin MetHb concentration sensitively.

Scharf proposed in his patent (U.S. Pat. No. 5,830,137) the use of the green wavelength region for the third wavelength. The absorption coefficient of every kind of hemoglobin, as shown in FIG. 11, is considerably large in the yellow and green wavelength regions. The absorption coefficients of the oxyhemoglobin O2Hb in the wavelength region of 500 nm to 620 nm are at least 10 times as large as those at 660 nm. Light having passed through the blood is very weak, and the measurement at good S/N ratio is very difficult.

SUMMARY OF INVENTION

Accordingly, an object of the present invention is to provide an apparatus for determining concentrations of hemoglobins which, using an orange or red orange wavelength region for the third wavelength in addition to the near-infrared and red wavelength regions, which are conventionally used, can detect a change of the transmitted light by a change of the methemoglobin MetHb at good S/N ratio, and can easily discriminate between the methemoglobin Metab and the deoxyhemoglobin RHb, and hence can perform a proper measurement of methemoglobin MetEb.

The present invention provides an apparatus for determining concentrations of hemoglobins according to the present invention comprises:

a light source which emits at least three different light rays: that is, light in a near-infrared wavelength region as a first wavelength, light in a red wavelength region as a second wavelength, and light in a red orange wavelength region as a third wavelength;

light-receiving means for receiving light that has originated from the light source and has passed through or has been reflected by a living tissue;

attenuation ratio processing means which processes an attenuation ratio Φ between the light rays of the wavelengths in accordance with a change in a received-light output signal in each wavelength output from the light-receiving means as a result of pulsation of blood; and concentration ratio processing means which processes at least concentration ratios of oxyhemoglobin and that of methemoglobin.

In this case, the concentration ratio processing means can be configured so as to process a proportion between an ever-changing concentration of oxyhemoglobin, an ever-changing concentration of methemoglobin, and an ever-changing concentration of methylene blue when medical treatment of methemoglobinemia is performed by administration of methylene blue into a living tissue, provided that at least a concentration of deoxyhemoglobin and that of carboxyhemoglobin remains unchanged.

Preferably, the apparatus can also be configured so as to further comprise oxygen saturation processing means which processes a functional oxygen saturation or a fractional oxygen saturation on the basis of an output from the concentration ratio processing means.

Preferably, the apparatus can also be configured so as to further comprise alarm display means for displaying an alarm in accordance with a level of the concentration ratio of methemoglobin obtained by the concentration ratio processing means.

Preferably, the apparatus can also be configured so as to further comprise event input means for enabling event entry at the time of occurrence of event information about medical treatment or about a patient; and storage means for storing a time at which input information is entered by way of the event input means, the event information, and a result of processing performed by the concentration ratio processing means.

Preferably, the apparatus can also be configured so as to further comprise display means which provides the processing result in the form of a trend display and which provides the event information stored in the storage means in the form of the trend display at a corresponding time.

Preferably, the apparatus can also be configured so as to further comprise an interface which transmits the event information, the time, and the processing result, all being stored in the storage means, to an external device.

The present invention also provides an apparatus for determining concentrations of hemoglobins, comprising:

a light source for emitting a plurality of light rays of different wavelengths;

light-receiving means for receiving light which has originated from the light source and has passed through or been reflected by a living tissue;

calibration value input means for entering a concentration of at least one type of light-absorbing material in blood;

attenuation ratio processing means for processing an attenuation ratio Φ between the light rays of the wavelengths, on the basis of a change in a received-light output signal in each wavelength output from the light-receiving means as a result of pulsation of blood; and concentration ratio processing means for processing a concentration ratio of oxyhemoglobin and a concentration ratio of methemoglobin, on the basis of an output from the attenuation ratio processing means and of the concentration of light-absorbing material input by way of the calibration value input means. Further, the apparatus can be also configured so as to comprise storage means for storing data pertaining to the attenuation ratio Φ; and concentration ratio processing means for retroactively re-processing at least a concentration ratio of oxyhemoglobin and a concentration ratio of methemoglobin, through use of the data stored in the storage means and the concentrations of light-absorbing materials in blood entered by way of the calibration value input means.

The present invention also provides an apparatus for determining concentrations of hemoglobins, comprising:

a light source for emitting a plurality of light rays of different wavelengths;

light-receiving means for receiving light which has originated from the light source and has passed through or been reflected by a living tissue;

attenuation ratio processing means for processing an attenuation ratio Φ between the light rays of the wavelengths, on the basis of a change in a received-light output signal in each wavelength output from the light-receiving means as a result of pulsation of blood;

concentration ratio processing means for processing at least a proportion between a concentration of oxyhemoglobin and a concentration of methemoglobin, on the basis of an output from the attenuation ratio processing means; and select means for instructing process of a concentration ratio of methemoglobin, wherein, when the select means has not yet instructed process of a concentration ratio of methemoglobin, the concentration ratio processing means processes a concentration ratio of at least oxyhemoglobin, on the basis of variations in received-light output signals output as a result of the light-receiving means having received at least two different light rays which have originated from the light source and have passed through or been reflected by the living tissue; and wherein, when the select means has instructed process of a concentration ratio of methemoglobin, the concentration ratio processing means processes concentration ratios of at least oxyhemoglobin and methemoglobin on the basis of variations in received-light output signals output as a result of the light-receiving means having received at least three different light rays which have originated from the light source and have passed through or been reflected by the living tissue The present invention also provides an apparatus for determining concentrations of hemoglobins, comprising:

a light source for emitting a plurality of light rays of different wavelengths;

light-receiving means for receiving light which has originated from the light source and has passed through or been reflected by a living tissue;

attenuation ratio processing means for processing an attenuation ratio Φ between the light rays of the wavelengths, on the basis of a change in a received-light output signal in each wavelength output from the light-receiving means as a result of pulsation of blood;

concentration ratio processing means for processing at least a proportion between a concentration of oxyhemoglobin, a concentration of deoxyhemoglobin, and a concentration of methemoglobin, on the basis of an output from the attenuation ratio processing means; and display means for displaying the determined value of oxyhemoglobin, that of deoxyhemoglobin, and that of methemoglobin through use of two-dimensional coordinates.

Preferably, the apparatus for determining concentrations of hemoglobins can be configured such that the light source emits at least three light rays of different wavelengths: that is, light in a near-infrared wavelength region as a first wavelength, light in a red wavelength region as a second wavelength, and light in a red orange as a third wavelength.

An apparatus for determining concentrations of hemoglobins according to the present invention comprises:

a light source which emits at least three different light rays: that is, light in a near-infrared wavelength region as a first wavelength, light in a red wavelength region as a second wavelength, and light in a red orange wavelength region as a third wavelength;

light-receiving means for receiving light that has originated frog the light source and has passed through or has been reflected by a living tissue;

attenuation ratio processing means which processes an attenuation ratio Φ between the light rays of the wavelengths in accordance with a change in a received-light output signal in each wavelength output from the light-receiving means as a result of pulsation of blood;

concentration ratio comparison means which processes at least a proportion of the concentration of oxyhemoglobin, that of carboxyhemoglobin, and that of methemoglobin; and switch means for causing the concentration ratio processing means to selectively process a ratio of the concentration of carboxyhemoglobin to that of methemoglobin.

In this case, the apparatus for determining concentrations of hemoglobins can be constructed such that a predetermined threshold is set for an attenuation ratio to be processed by the attenuation ratio processing means; and there is provided display means for displaying an alarm when an attenuation ratio processed for the hemoglobin to which the switch means has been switched has exceeded the threshold value.

The present invention also provides an apparatus for determining concentrations of hemoglobins according to the present invention comprises;

a light source which emits at least three different light rays: that is, light in a near-infrared wavelength region as a first wavelength, light in a red wavelength region as a second wavelength, and light in a red orange wavelength region as a third wavelength;

light-receiving means for receiving light that has originated from the light source and has passed through or has been reflected by a living tissue;

attenuation ratio processing means which processes a ratio of an attenuation associated with concentrations of carboxyhemoglobin and methemoglobin on the basis of a variation of a received-light output signal in each wavelength output from the light-receiving means as a result of pulsation of blood; and display means for displaying an alarm when at least either a processed attenuation ratio of carboxyhemoglobin or a processed attenuation ratio of methemoglobin has exceeded a range of a predetermined threshold value, the threshold value being set for an attenuation ratio of carboxyhemoglobin and an attenuation ratio of methemoglobin which are to be processed by the attenuation ratio processing means.

Preferably, at least the first wavelength is selected from a near-infrared wavelength region of 790 to 1000 nm; the second wavelength is selected from a red wavelength region of 640 to 675 nm; and the third wavelength is selected from a red orange wavelength region of 590 to 660 nm.

Particularly, the third wavelength is preferably set to 621 nm.

The present invention also provides an apparatus for determining concentrations of hemoglobins, comprising:

a light source for emitting a plurality of light rays of different wavelengths;

light-receiving means for receiving light which has originated from the light source and has passed through or been reflected by a living tissue;

input means for entering a reference time;

attenuation ratio processing means for processing an attenuation ratio Φ between the light rays of the wavelengths, on the basis of a change in a received-light output signal in each wavelength output from the light-receiving means as a result of pulsation of blood; and concentration variation processing means for processing variation in the concentration of at least either carboxyhemoglobin or methemoglobin having arisen since the reference time entered by way of the input means.

By means of this configuration, a physician who performs medical treatment performs an input operation for causing the apparatus to recognize, e.g., when the treatment is initiated, as a reference time by way of the input means. There can be processed variation in the concentration of at least either carboxyhemoglobin or methemoglobin having arisen since the reference time input by way of the input means.

Moreover, the input means corresponds to calibration value input means; and the concentration variation processing means processes variation in a concentration having arisen since the reference time, by inputting a tentative value by way of the calibration value input means as a concentration of light-absorbing material in blood.

As a result, provided that time when a medical treatment has been initiated is taken as a reference time, there can be processed variation in the concentration of carboxyhemoglobin or methemoglobin having arisen since the reference time, by inputting a tentative value by way of the calibration value input means as a concentration of light-absorbing material in blood.

DETAILED DESCRIPTION OF PREFERRED EMBODIMENT

Principle of the Invention

Figure 9:
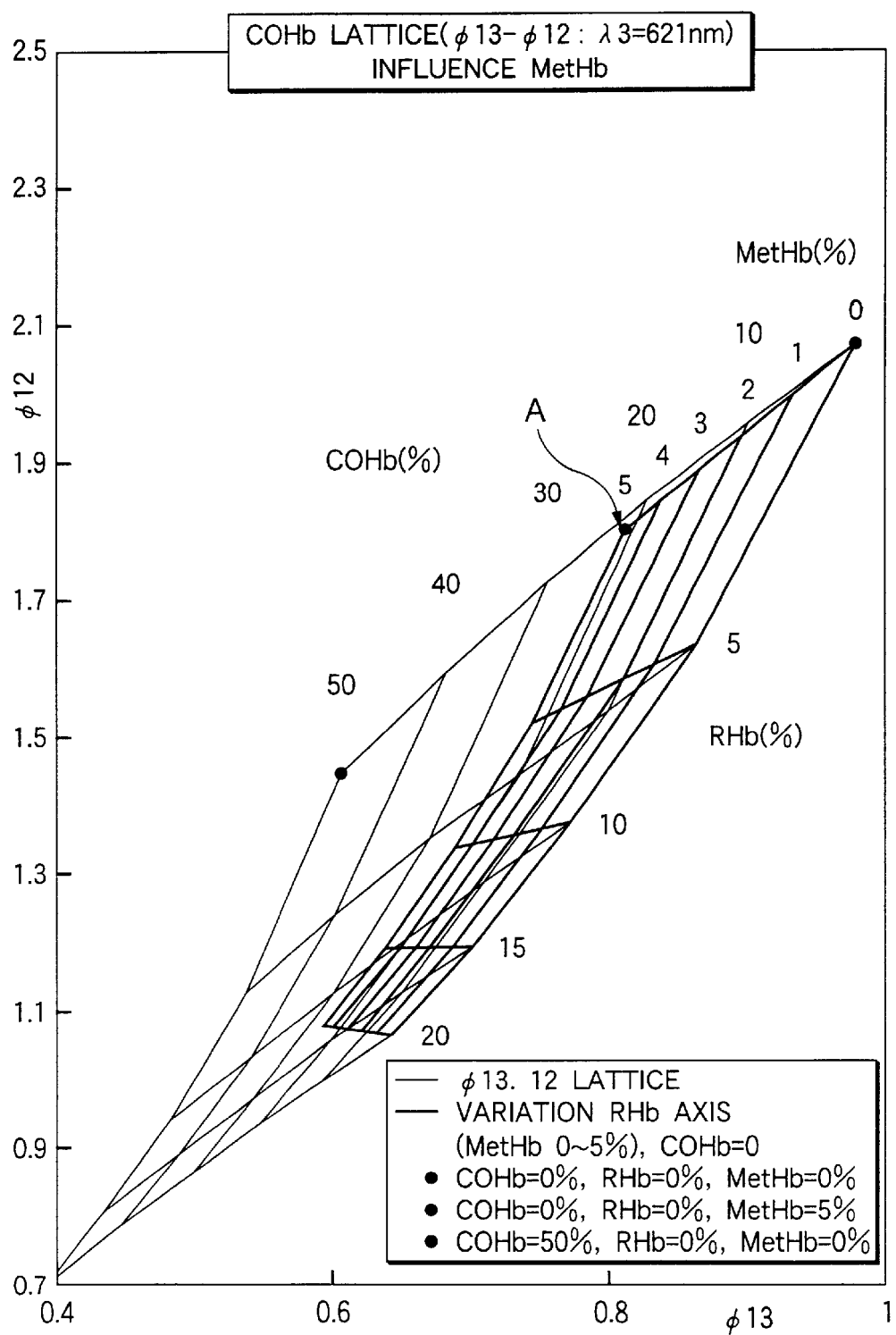
FIG. 9 is a characteristic graph showing the relationship between two attenuation ratios $\Phi 12$ and $\Phi 13$ at optical wavelengths applied to the hemoglobin concentration determining apparatus according to the present invention.
Figure 10:
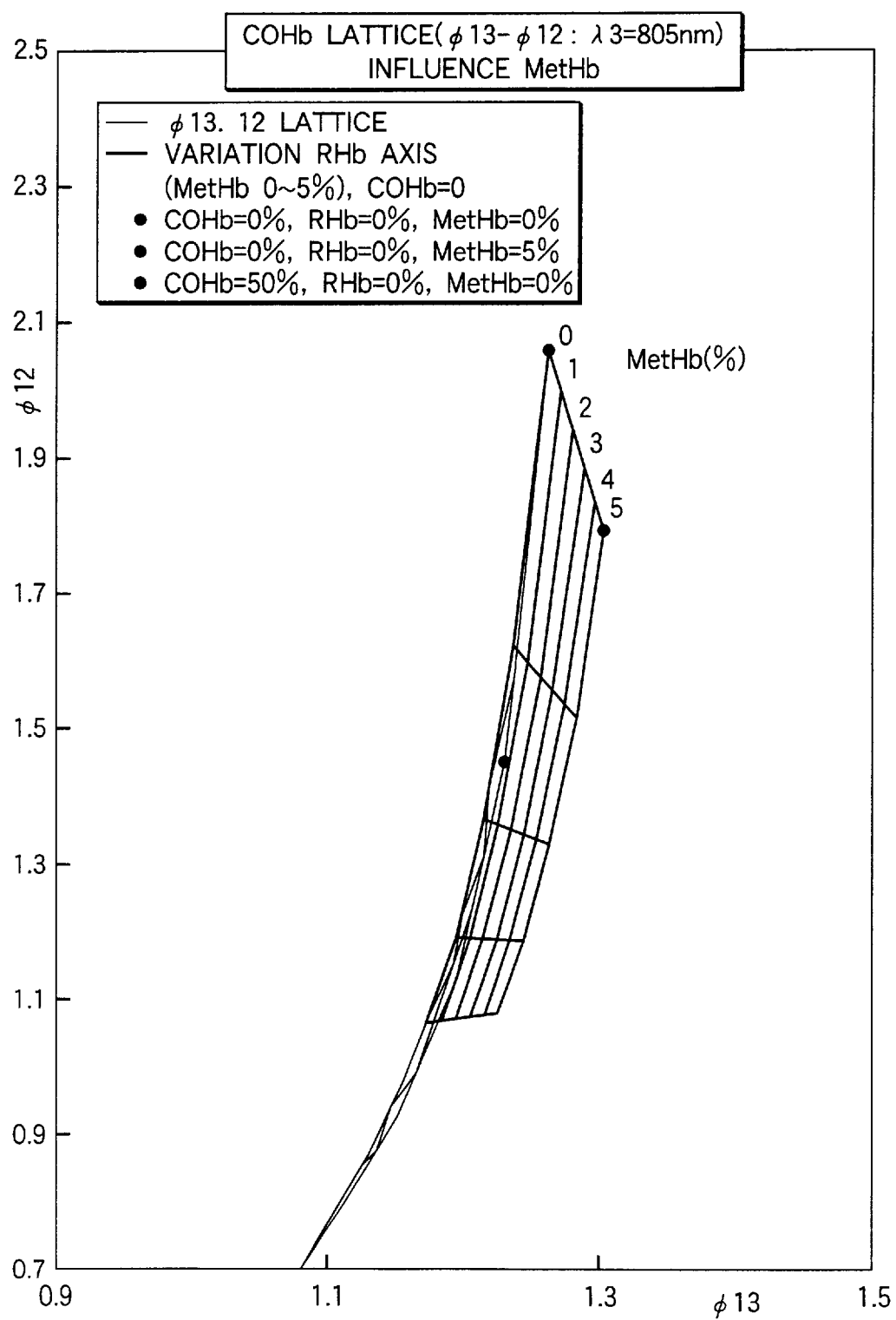
FIG. 10 is a characteristic graph showing the relationship between two attenuation ratios $\Phi 12$ and $\Phi 13$ at optical wavelengths at the hemoglobin concentration determining apparatus for which a third wavelength of 805 nm in a near-infrared wavelength region has been set.
Figure 11:
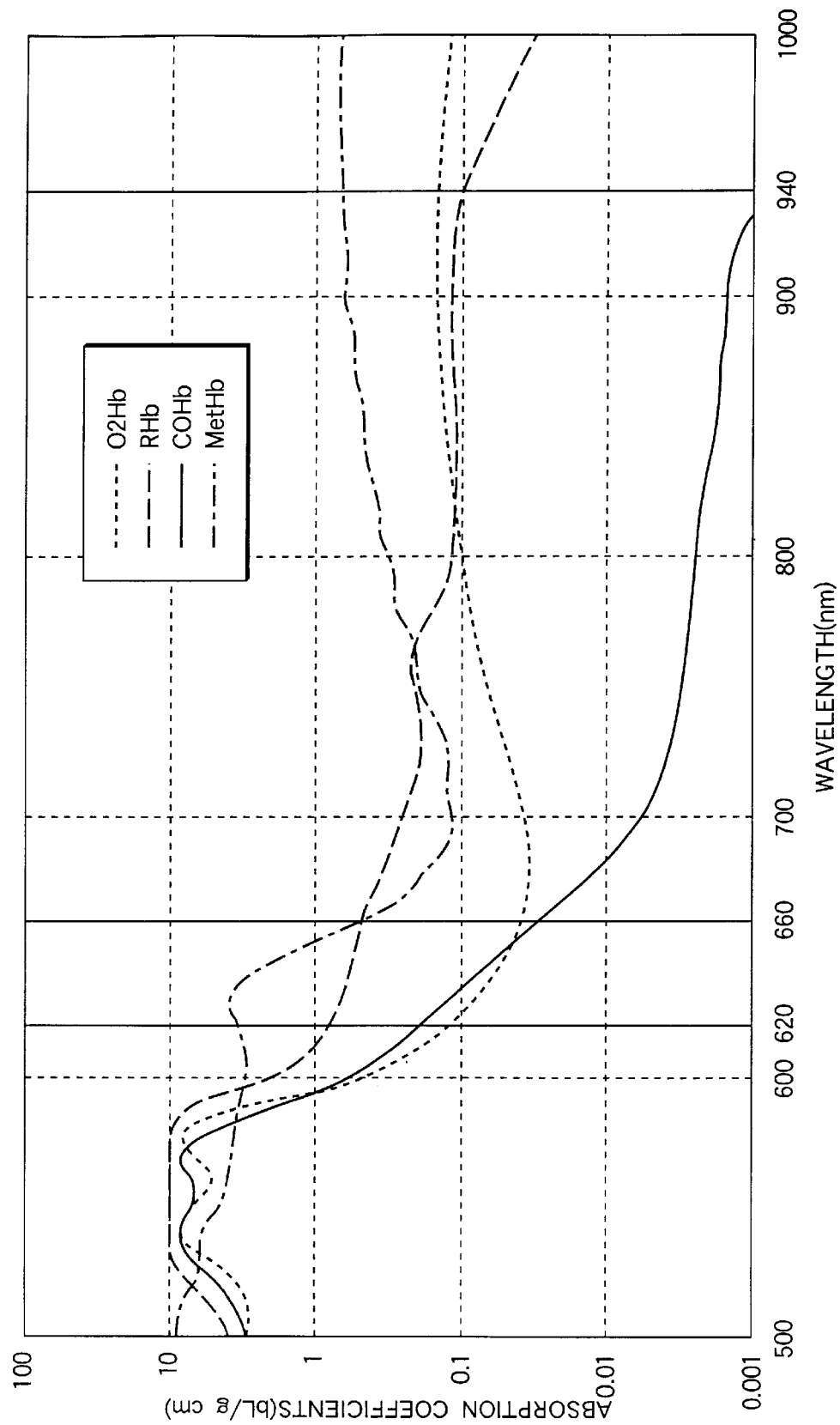
FIG. 11 shows characteristic curves showing the relationship between absorption coefficients and wavelength.

The inventors of the present patent application discovered the following fact: when any of the orange or red orange wavelengths is used for the third wavelength, in addition to the near-infrared and red wavelengths, which are conventionally used, a change of the transmitted light which results from a change of the methemoglobin MetHb is detected at good S/N ratio, it is easy to discriminate between the methemoglobin MetHb and the deoxyhemoglobin RHb, and hence it is possible to properly measure the methemoglobin MetHb.

Where the near-infrared wavelength is 940 nm, the red wavelength is 660 nm, the near-infrared wavelength is 805 nm, and the orange wavelength is 621 nm, the values of the concentration ratios of deoxyhemoglobin RHb and methemoglobin MetHb $\Phi 12$ and $\Phi 13$ were investigated. From the investigation, it was seen that at the infrared wavelength of 805 nm, the directions in which $\Phi 12$ and $\Phi 13$ change are coincident with each other for the changes of both the deoxyhemoglobin RHb and the methemoglobin MetHb. In this state, it was found that it was difficult to discriminate between the deoxyhemoglobin RHb and the methemoglobin MetHb as shown in FIG. 10. In the case of the orange wavelength of 621 nm, the orthogonality of a changing direction of the deoxyhemoglobin RHb and a changing direction of the methemoglobin MetHb, increases. Accordingly, the discrimination is easy as shown in FIG. 9. This fact was found and confirmed.

The peak of light absorption of methylene blue used for medical treatment of methemoglobinemia appears at a wavelength of 668 nm. The third wavelength of 621 nm is distant from the light-absorption peak of methylene blue. Hence, it has been ascertained that influence of light absorption imposed on measurement by methylene blue is lessened and that methemoglobin can be measured with smaller errors during medical treatment.

Methemoglobinemia resulting from the concentration of methemoglobin (MetHb) in blood has hitherto been known as arising from the following causes:

(1) Congenital reductase deficiency
(2) Nitrogen monoxide inhalation medical treatment
(3) Administration of a vasodilator drug, such as nitrite
(4) Administration of topical anesthetic, such as prilocaine
(5) Poisoning caused by an aniline-based agricultural chemical Of the causes of methemoglobinemia, cause (1) is found in a newborn. If the concentration of methemoglobin MetHb in blood exceeds 10%, the skin becomes darkish, and blood becomes reddish brown. No improvement is observed after oxygen inhalation. If bedside-sampled blood is found to turn reddish brown instead of turning red when dropped on filter paper, a patient will be diagnosed as methemoglobinemia. Sampling poses a heavy burden on a newborn, because of small blood volume. Hence, ability to determine presence of methemoglobin MetHb in blood in a noninvasive manner would yield a considerably great benefit.

In the cases of causes (2), (3), and (4), a medical treatment performed on a patient causes generation of methemoglobin MetHb in the blood. A physician performing the medical treatment is afraid that methemoglobin MetHb might generate in blood. Therefore, the doctor frequently samples blood and determines a concentration of methemoglobin MetHb with a carbon monoxide oximeter or cuts down doses of medication, thus preventing a rise in the concentration of methemoglobin MetHb in blood. A monitor which continuously determines the concentration of methemoglobin MetHb in blood and issues an alarm when the blood methemoglobin metHb concentration exceeds a certain level is very useful in such a situation.

If a patient is found unconscious, cause (5) follows one of two scenarios; that is, a situation in which the patient is known to have ingested an agricultural chemical, and another situation in which the patient is not known to be even chemical poisoning. If presence of methemoglobin MetHb in blood is found when a patient is carried into an ambulance, the patient can have early treatment. Hence, detection of methemoglobin MetHb can contribute not only to an improvement in prognosis of the patient but also to a saving of medical expenses.

As mentioned above, there has been no method of continuously measuring the concentration of methemoglobin MetHb in blood. In many cases, presence of methemoglobin MetHb in blood remains unknown until blood is sampled when an anomaly in the patient is found such as cyanosis. Against such a backdrop, even when the concentration of methemoglobin MetHb in blood is not determined precisely, a sufficient clinical efficacy can be achieved by following means:by indicating "Present/Absent" of a blood methemoglobin MetHb concentration with 5% as the borderline of the present/absent or by indicating methemoglobin MetHb in three levels of "Absent/Possible/Perilous."

Accordingly, another object of the present invention is to provide an apparatus for determining a concentration of hemoglobin employing a hemoglobin concentration indication method capable of displaying the concentration of methemoglobin MetHb determined by the hemoglobin concentration determination apparatus, in a clinically-effective and simple manner.

The present invention can be configured so as to be able to enhance the reliability of subsequent measurement values, by calibrating errors caused by the influence of a tissue or other light-absorbing materials in blood through entry of a measurement value determined by a blood collection method. More specifically, a gold standard for determining a ratio of concentration of methemoglobin MetHb in blood corresponds to blood sampling measurement using a carbon monoxide oximeter. Calibration using such a highly-reliable measurement value enables an improvement in the accuracy of a measurement value.

As mentioned above, causes (2), (3), and (4) attributable to generation of methemoglobin MetHb in blood cause methemoglobin MetHb to arise in blood as a result of a medical treatment being performed on a patient. If variations in the concentration of methemoglobin MetHb in blood in subsequent processes of a medical treatment can be continuously and accurately monitored by effecting a calibration before or during a medical treatment, the safety of the medical treatment can be improved to a much greater extent. In this case, providing the hemoglobin concentration determination apparatus with a storage function, a trend display, and a marker function, such as a function for marking initiation of oxygen inhalation, will facilitate a medical treatment of a patient having methemoglobinemia resulting from chemical poisoning, after transport to a hospital.

According to the present invention, the pulse oximeter using three wavelengths can be constructed so as to be able to determine the concentration of a selected substance by using a selected formula when an operator has selected either measurement of a concentration of methemoglobin MetHb or a concentration of carboxyhemoglobin COHb. For instance, if the wavelength of orange or red orange light is selected as a third wavelength, the concentration of carboxyhemoglobin COHb can be determined, as described in Japanese Patent Application Laid-Open No. 366152/2000 filed by the present inventor. Under a condition that carboxyhemoglobin COHb is absent, a concentration of methemoglobin MetHb can also be determined by combination of the same wavelength, as described previously.

More specifically, a patient who has become unconscious in an accident such as a fire is strongly suspected of having been subjected to carbon monoxide poisoning. For this reason, measurement of carboxyhemoglobin COHb can be selectively used at the site where first aid is administered. If the patient is known to have been subjected to poisoning resulting from an aniline-based agricultural chemical, measurement of methemoglobin MetHb is selectable. According to the principle on which the pulse oximeter is based, use of three wavelengths enables determination of a ratio of concentrations of three or fewer light-absorbing materials in blood. As in the case of the above-described situation, if an operator selects a target substance given that a certain material has no concentration, a ratio of concentrations of three or more light-absorbing materials in blood can be determined by use of three wavelengths with a modification being made to the formula, According to the present invention, the pulse oximeter using three wavelengths can be constructed so as to be able to indicate presence of abnormal hemoglobin in blood; that is, either methemoglobin MetHb or carboxyhemoglobin COHb. For instance, on condition that oxyhemoglobin $O_2Hb$ in blood is 100%, if 940 nm is selected for a first wavelength, 660 nm is selected for a second wavelength, and 621 nm is selected for a third wavelength, a change in attenuation ratio—which is obtained when an increase has arisen in only the Concentration of carboxyhemoglobin COHb—is expressed by $\Phi 13$ taken for the X axis, and a change in attenuation ratio—which is obtained when an increase has arisen in only the concentration of methemoglobin MetHb—is expressed by $\Phi 12$ taken for the Y axis. As shown in FIG. 9, even when an increase has arisen in the concentration of carboxyhemoglobin COHb or the concentration of methemoglobin MetHb, a drop arises in the attenuation ratio $\Phi 13$. In other words, point A shown in FIG. 9 arises in a situation of 95% oxyhemoglobin $O_2Hb$ and 5% methemoglobin MetHb as well as in a situation of 80% oxyhemoglobin $O_2Hb$ and 20% carboxyhemoglobin COHb.

As shown in FIG. 9, a certain threshold value is made for an attenuation ratio. When an attenuation ratio has exceeded the threshold value, it is possible that abnormal hemoglobin is present, although the abnormal hemoglobin is either carboxyhemoglobin COHb or methemoglobin MetHb. Particularly, when an unconscious patient is found in an emergency situation, if medical staff find abnormal hemoglobin is present in the patient's blood, the blood is immediately sampled to determine whether the abnormal hemoglobin is carboxyhemoglobin COHb or methemoglobin MetHb, thereby enabling immediate and accurate medical treatment. When the patient is under anesthesia, methemoglobin MetHb sometimes arises as a result of administration of a topical anesthetic or vasodilator. Alternatively, it is known that carboxyhemoglobin coHb can be generated when an inhalative narcotic reacts with a drying agent on rare occasions.

Thus, when the patient is under anesthesia, there is a potential risk of unintentional generation of methemoglobin MetHb or carboxyhemoglobin COHb. The related-art pulse oximeter cannot detect these hemoglobins. According to the present invention, generation of an abnormal hemoglobin, such as methemoglobin MetHb or carboxyhemoglobin COHb, is continuously monitored during anesthesia. If an abnormal hemoglobin has generated, an alarm sign can be displayed and inform an anesthesiologist of an anomaly in the patient. The anesthesiologist can sample blood to find which of the abnormal hemoglobins has generated, thereby enabling early treatment.

The present invention provides a processing method which can eliminate the influence on measurement of methemoglobin MetHb exerted by a methylene blue coloring agent which is a drug for treatment of a methemoglobinemia. In short, the intravenous administration of methylene blue is generally known as a treatment for methemoglobinemia. The methylene blue has a light-absorbing peak at a wavelength of 668 nm. If methylene blue is present in blood, neither a carbon monoxide oximeter nor a related-art pulse oximeter can perform an appropriate measurement operation using a wavelength in the vicinity of 660 nm. For this reason, there is no available method of continuously monitoring a therapeutic effect of reducing methemoglobin MetHb during a medical treatment using methylene blue. For this reason, the present invention enables appropriate measurement of the concentration of methemoglobin MetHb in blood with obviation of an influence on light absorption exerted by methylene blue.

The preferred embodiment of an apparatus for determining concentrations of hemoglobins, which is constructed according to the present invention, will be described with reference to the accompanying drawings.

Embodiments

Figure 1:
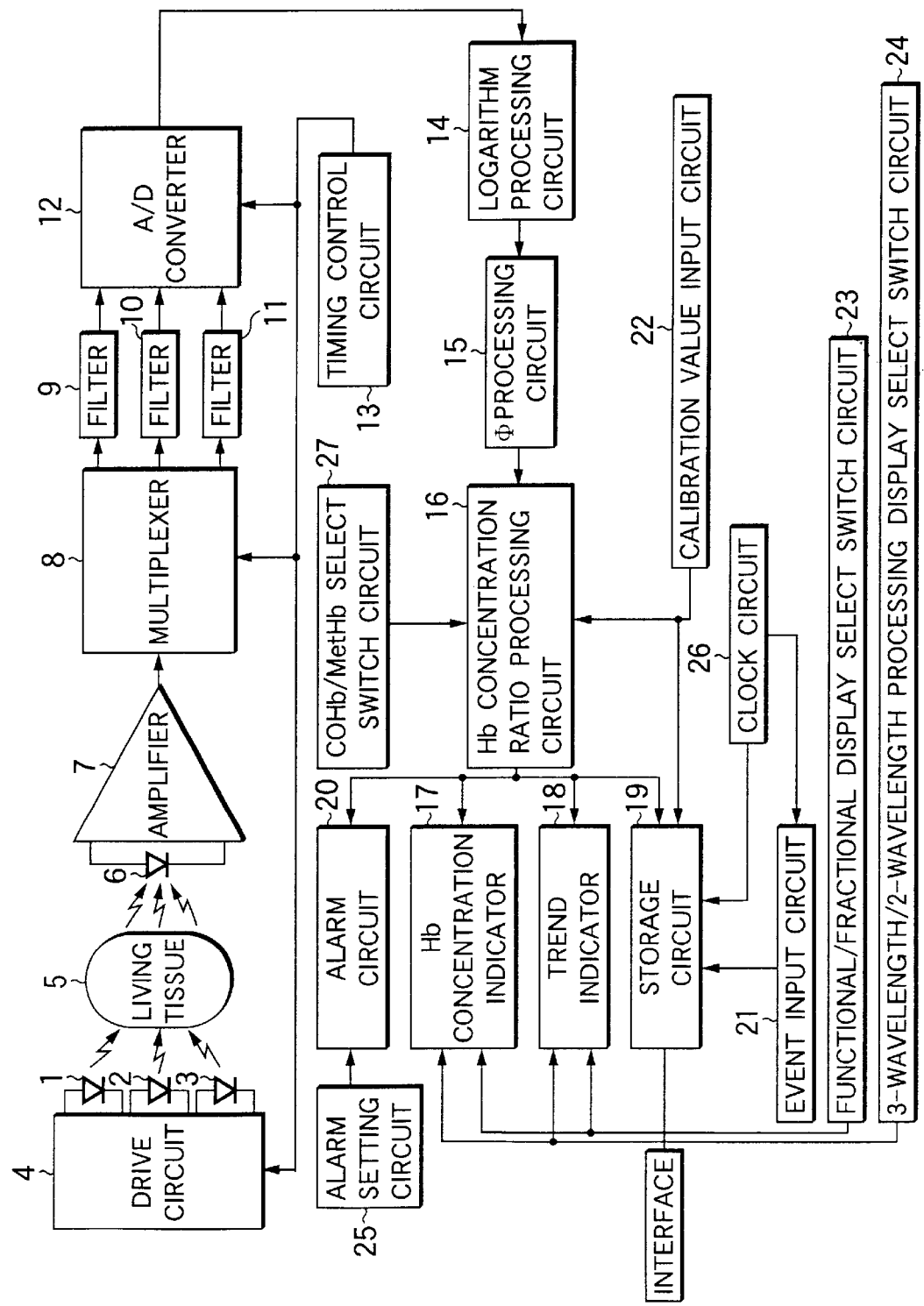
FIG. 1 is a schematic block diagram showing an embodiment of the configuration of an apparatus for determining concentrations of hemoglobins according to the present invention.

FIG. 1 is a block diagram showing a system arrangement of an apparatus for determining concentrations of hemoglobins constructed to the present invention. In FIG. 1, reference numerals 1, 2 and 3 indicate light emitting elements as light sources. Those elements 1, 2 and 3, respectively, emit near-infrared light of a first wavelength $\lambda 1$, which is any of 790 nm to 1000 nm, red light of a second wavelength $\lambda 2$, which is any of 640 nm to 675 nm, and orange or red orange light of a third wavelength $\lambda 3$, which is any of 590 nm to 660 nm. Those light emitting elements are driven by a drive circuit 4. The lights emitted from those elements 1, 2 and 3 transmit through a living tissue 5, and is received by a light receiving element 6 as light receiving means. The light receiving element 6 converts the lights into corresponding electrical signals. Those electrical signals are amplified by an amplifier 7, and applied to a multiplexer 8. The multiplexer then delivers respectively those signals to filters 9, 10 and 11, which are provided corresponding to the wavelengths of the lights.

Those filters 9 to 11 remove the high frequency components as noise from those signals, and send the resultant signals to an A/D converter 12, which in turns converts those signals into digital signals. Then, the digital signals are input to a logarithm processing circuit 14, a $\Phi$ processing circuit 15 as attenuation ratio processing means for processing attenuation ratios $\Phi$, and an Hb concentration ratio processing circuit 16 as hemoglobin Hb concentration ratio processing means. Reference numeral 13 indicates a timing control circuit 13. The timing control circuit sends necessary timing signals to the drive circuit 4, multiplexer 8 and A/D converter 12 to control the operations of those circuits.

The logarithm processing circuit 14 processes I1, I2, and I3 as the output signals of the A/D converter 12 to produce logarithms lnI1, lnI2 and lnI3 respectively. The $\Phi$ processing circuit 15 extracts the pulsating components from the logarithms lnI1, lnI2 and lnI3 obtained by the logarithm processing circuit 14, and processes $\Phi 12 = \Delta lnI1/\Delta lnI2$ and $\Phi 13 \cong \Delta lnI1/\Delta lnI3$. The Hb concentration ratio processing circuit 16 solves simultaneous equations describing the ratios $\Phi$, and obtains concentration ratios of oxyhemoglobin O2Hb, deoxyhemoglobin RHb and Methemoglobin MetHb.

The processing expression in the Hb concentration ratio processing circuit 16 is as given by the following expression.

$$\Phi 12 = \Delta A1/\Delta A2 = \sqrt{[(Eo1O2Hb+Er1RHb+Em1MetHb)\{(Eo1O2Hb+Er1RHb+Em1MetHb)+F\}]}/\sqrt{[(Eo2O2Hb+Er2RHb+Em2MetHb)\{(Eo2O2Hb+Er2RHb+Em2MetHb)+F\}]} \quad (4)$$

$$\Phi 13 = \Delta A1/\Delta A3 = \sqrt{[(Eo1O2Hb+Er1RHb+Em1MetHb)\{(Eo1O2Hb+Er1RHb+Em1MetHb)+F\}]}/\sqrt{[(Eo3O2Hb+Er3RHb+Em3MetHb)\{(Eo3O2Hb+Er3Hb+Em3MetHb)+F\}]} \quad (4')$$

In the above expressions, RHb is a concentration ratio of the deoxyhemoglobin, O2Hb is a concentration ratio of oxyhemoglobin, and MetHb is a concentration ratio of methemoglobin. Eoi (i=1,2,3) is an absorption coefficient of the oxyhemoglobin O2Hb. Eri (i=1.2,3) is an absorption coefficient of the deoxyhemoglobin RHb. Emi(i=1,2.3) is an absorption coefficient of the methemoglobin MetHb. F is a scattering coefficient. i=1, 2, 3 represent wavelengths $\lambda 1, \lambda 2, \lambda 3$. Those coefficients Eoi, Eri, Eci and F are known. Accordingly, the concentration ratios of the oxyhemoglobin O2Hb, the deoxyhemoglobin RHb and the methemoglobin MetHb can be obtained in a manner that $\Phi 12 = \Delta 1/\Delta 2$ and $\Phi 13 = \Delta 1/\Delta A3$ are measured, the measured ones are substituted for the simultaneous equations, and those equations are solved.

While the concentration ratios of the oxyhemoglobin O2Hb, the deoxyhemoglobin RHb and the methemoglobin MetHb are obtained from $\Phi 12$ and $\Phi 13$ by solving the simultaneous equations, the ratios may be obtained by referring to a table, which is prepared in advance by using processes or experiment results.

Signals representing concentration ratios of oxyhemoglobin O2Hb, deoxyhemoglobin RHb and methemoglobin MetHb, which are processed by the above-mentioned processing process in the Hb concentration ratio processing circuit 16, are input to an Hb concentration indicator 17 as hemoglobin Hb concentration display means, a trend indicator 18 as trend display means, a storage circuit 19 as storage means, and an alarm circuit 20 as alarm display means. In this case, the Hb concentration indicator 17, as shown in FIGS. 2 to 5, displays an arterial oxygen saturation SpO2 and a methemoglobin MetHb concentration.

Figure 2:
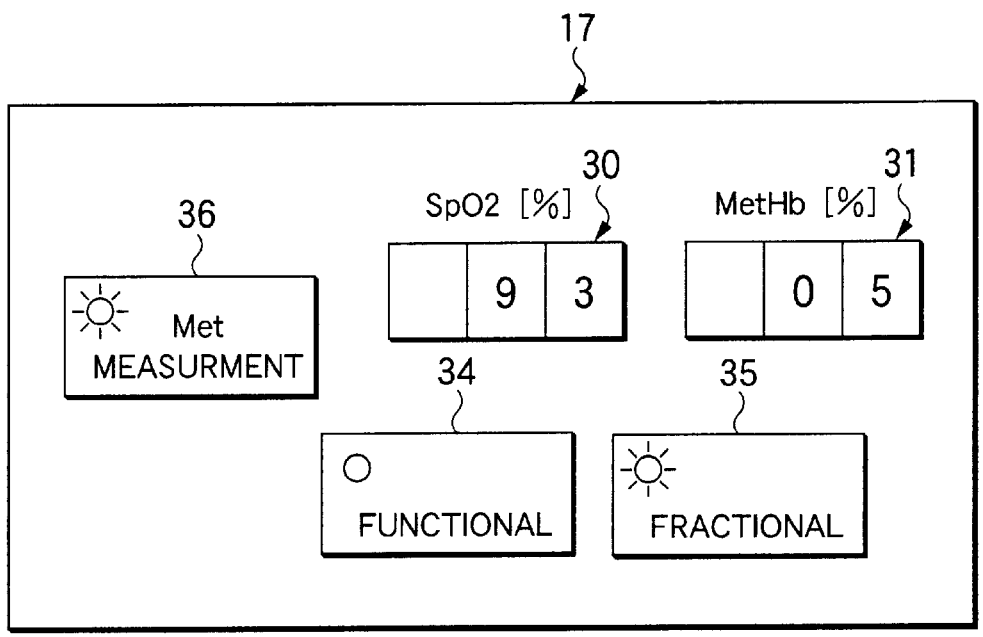
FIG. 2 is a descriptive view showing an example of configuration of a hemoglobin Hb concentration indicator shown in FIG. 1.

FIG. 2 exemplarily shows an arrangement of the Hb concentration indicator 17. In the display arranged as shown in FIG. 2, SpO2(%)=O2Hb/(O2Hb+RHb) (%) as a functional oxygen saturation or SpO2(%)=O2Hb/(O2Hb+RHb+MetHb) (%) as a fractional oxygen saturation is selected by a functional/fractional display select switch circuit 23 (see FIG. 1), and the selected one is displayed. Specifically, the display, as shown, contains an oxygen saturation SpO2 (%) numerical display section 30 and a MetHb concentration (%) numerical display section 31. The display further contains a functional select switch/select status display section 34 and a fractional select switch/select status display section 35, which are provided in association with the oxygen saturation SpO2 (%) numerical display section 30. The "functional oxygen saturation" or "fractional oxygen saturations" is selected and the selected one is displayed by use of the related section 34 or 35.

A numerical value to be displayed in the oxygen saturation SpO2 (%) numerical display section 30 is the one processed using three wavelengths or two wavelengths of red and near-infrared lights as in the conventional case, which is selected by 3-wavelength/2-wavelength processing display select switch circuit 24 (FIG. 1). In this case, to display the selected numerical value, MetHb determination button 36 is used. When the MetHb determination button 36 is turned on, concentrations of various types of hemoglobins inclusive of Methemoglobin may be measured using three wavelengths When it is turned off, an oxygen saturation (SpO2) may be measured as in the conventional manner using two wavelengths.

Figure 3:
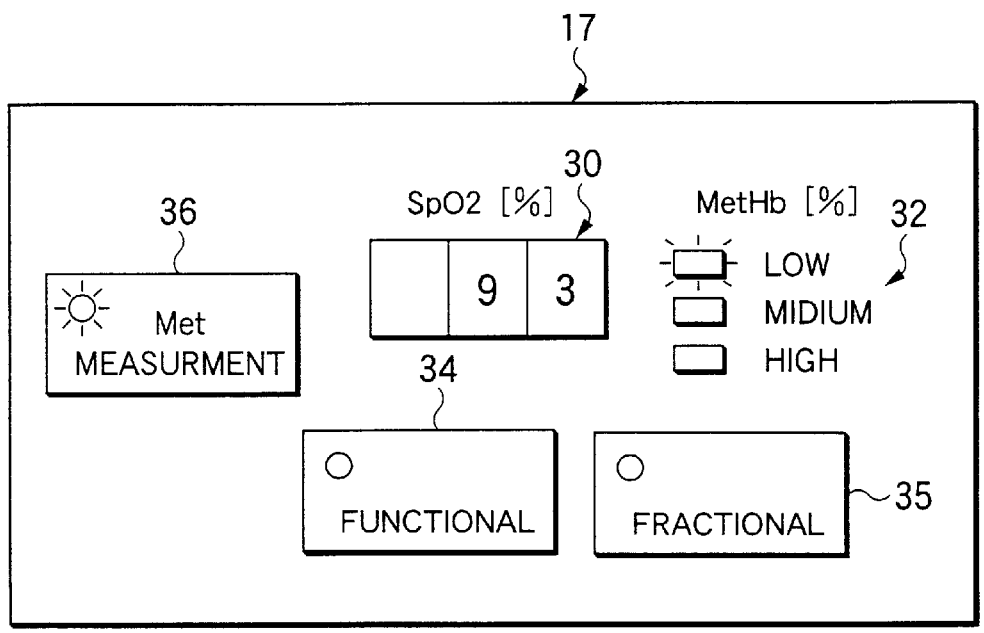
FIG. 3 is a descriptive view showing another example of configuration of a hemoglobin Hb concentration indicator shown in FIG. 2.

FIG. 3 shows another display arrangement of the Hb concentration indicator 17. In the display arranged as shown in FIG. 3, the fractional SpO2 (%) is displayed in the oxygen saturation SpO2 (%) numerical display section 30. The MetHb concentration (%) is indicated in any of three dangerous levels by a dangerous level indicator 32. Two levels may be used in lieu of three levels, for the purpose of a dangerous indication of the MetHb concentration. The remaining display arrangement is the same as that of the FIG. 2 one. No further description of it will be given here, while like portions are indicated by like reference numerals in FIG. 2.

Figure 4:
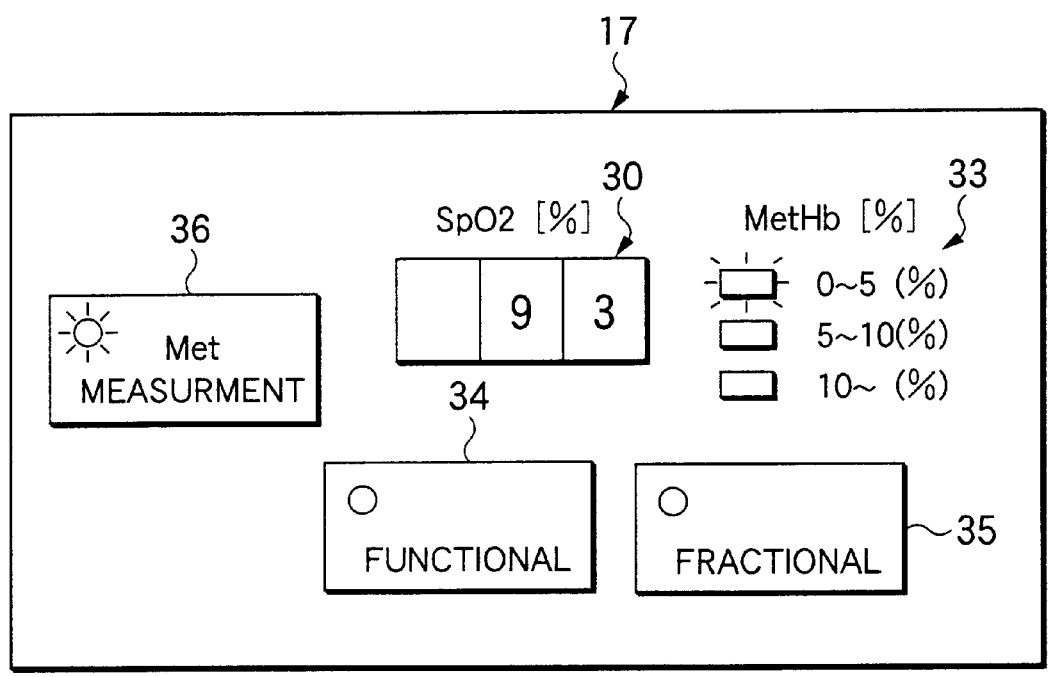
FIG. 4 is a descriptive view showing still another example of configuration of a hemoglobin Hb concentration indicator shown in FIG. 2.

FIG. 4 shows yet another display arrangement of the Hb concentration indicator 17. In the display arranged as shown in FIG. 4, a dangerous level indicator 33 is used for indicating a dangerous level of the MetHb concentration (%). In the dangerous level indicator 33, three dangerous levels shown in FIG. 3 are expressed in terms of numerical values. The remaining display arrangement is the same as that of the FIG. 2 one. No further description of it will be given here, while like portions are indicated by like reference numerals in FIG. 2.

Figure 5A:
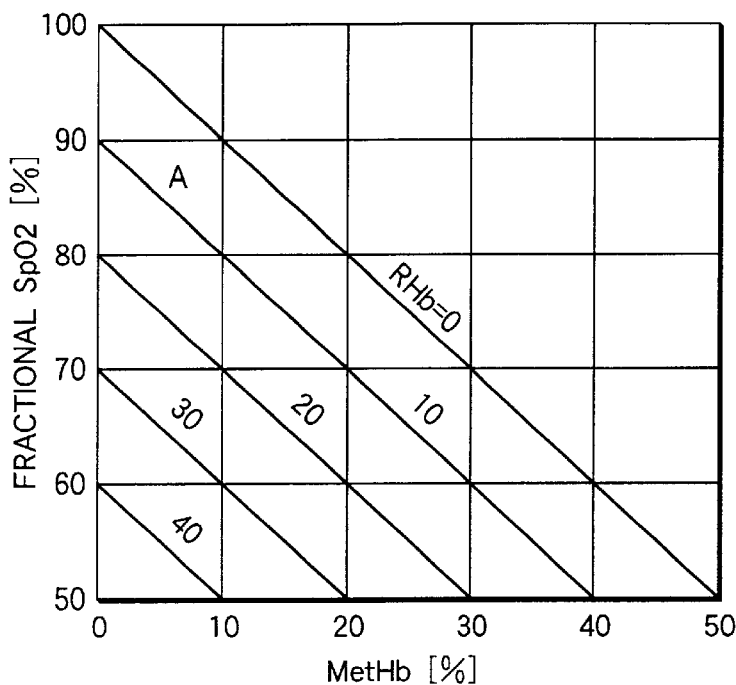
FIGS. 5(A) and 5(B) are descriptive view showing different example configurations of the hemoglobin Hb concentration indicator shown in FIG. 1, the configurations of which provide different displays.
Figure 5B:
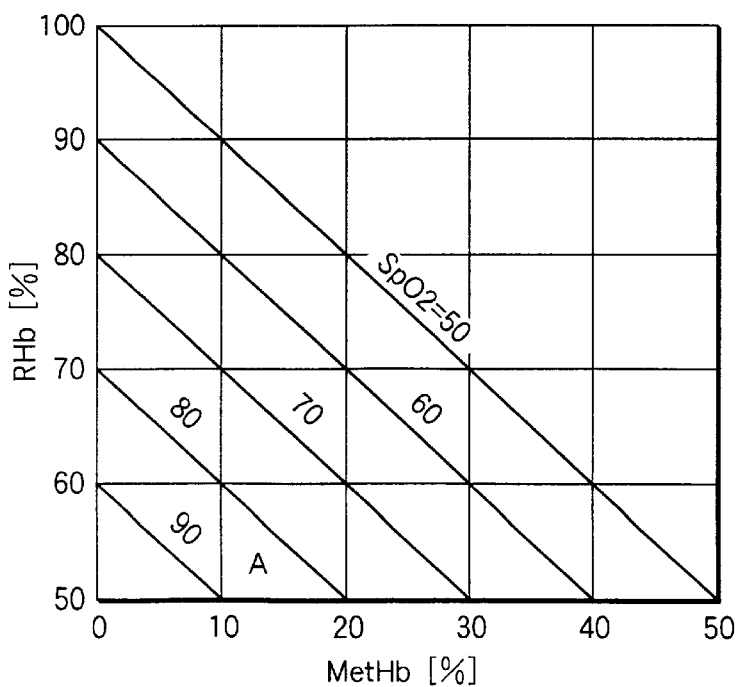

A display of the Hb concentration indicator 17 may also be designed as shown in FIGS. 5(A) and 5(B). In the display of FIG. 5(A), the abscissa represents the methemoglobin concentration, the ordinate represents the fractional oxygen saturation (oxyhemoglobin concentration), and the oblique line represents the deoxyhemoglobin concentration. The display thus designed visually presents three kinds of concentrations at a time. In the FIG. 5(A) display, a point A indicates that the methemoglobin concentration is 10%, the fractional oxygen saturation (oxyhemoglobin concentration) is 85%, and the deoxyhemoglobin concentration is 5%. A display designed differently from the just-mentioned one is shown in FIG. 5(B). In this display, the abscissa represents the methemoglobin concentration, the ordinate represents the deoxyhemoglobin concentration, and the oblique line represents the fractional oxygen saturation (oxyhemoglobin concentration). The display also visually presents three kinds of concentrations at a time by use of the X-Y coordinates.

In FIG. 1, the alarm circuit 20 generates an alarm by light, sound, a message or the like when a concentration of methemoglobin MetHb is higher than a value set by an alarm setting circuit 25. The alarm by light may be realized in the form of the lighting of an alarm lamp, the flickering of the lamp for indicating a dangerous level of the MetHb concentration, the flickering of the MetHb concentration (%) indicator or the like. The alarm by sound may be realized by an alarm sound representing the presence of MetHb. In this a case, the MetHb concentration may be informed by varying the sound volume or the sound interval in accordance with its concentration. The sound volume or interval may be varied continuously in accordance with the concentration or intermittently in accordance with a dangerous level. Additionally, a sound synchronous with a pulsation may be changed in accordance with the MetHb concentration. In this case, frequency of the sound or sounding duration may be changed in accordance with the presence of MetHb. In FIG. 1, reference numeral 26 designates a clock circuit for clock operating the storage circuit 19.

Figure 6A:
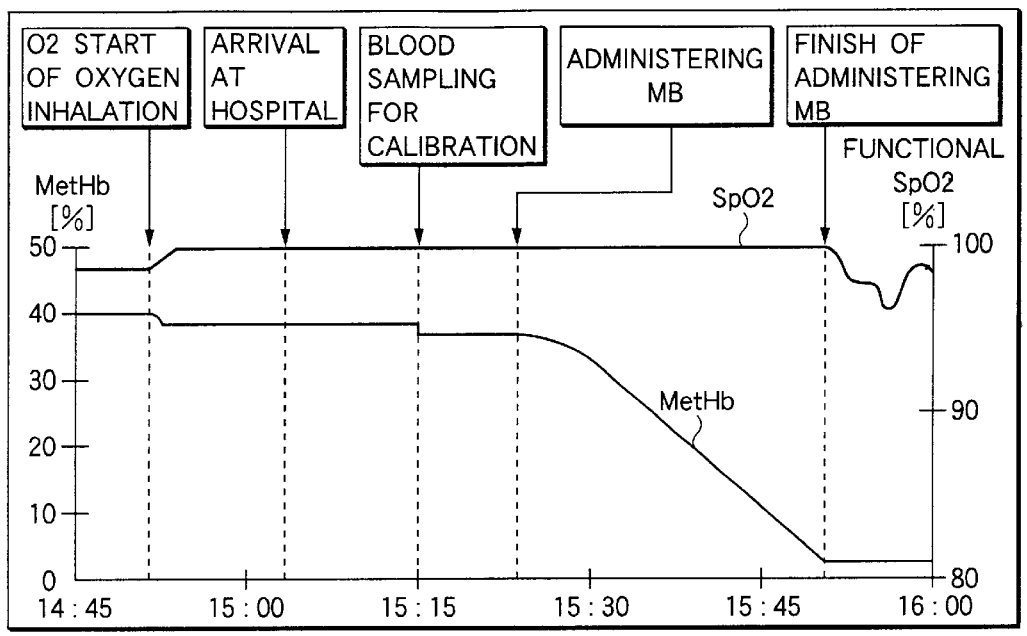
FIGS. 6(A) and 6(B) are descriptive views showing examples of configurations for the trend indicator shown in FIG. 1, the configurations of which provide different displays.
Figure 6B:
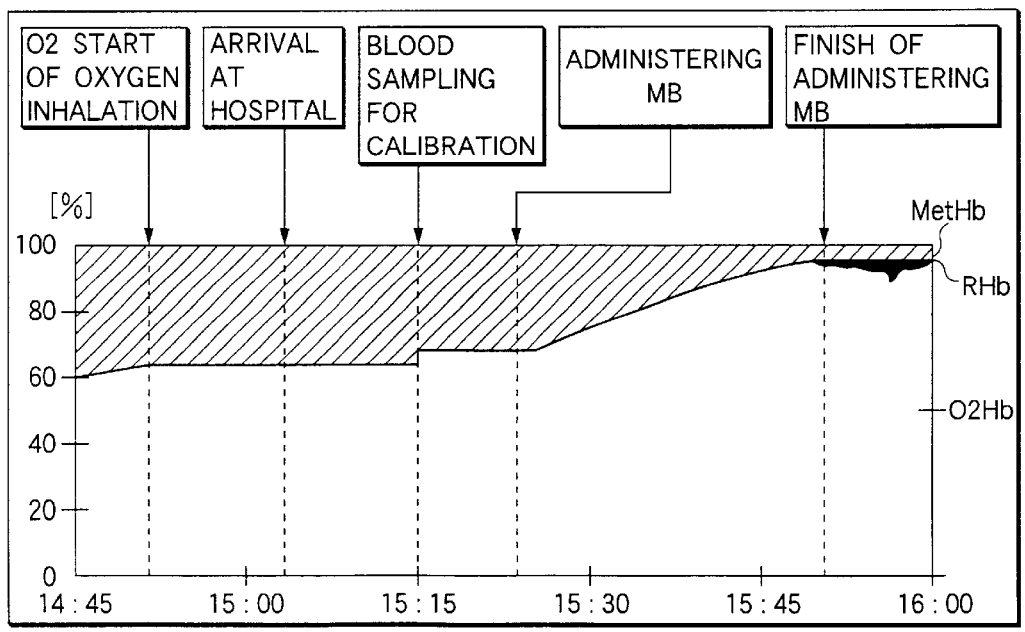

A further display of the trend indicator 18, which may be a liquid crystal display unit, is arranged as shown in FIGS. 6(A) and 6(B). The display visually presents trends of SpO2 (%) and MetHb concentration (%). When medical treatment is applied to for example, a methemoglobinemia patient caused by a chemical poisoning, information on the patient or the treatment is input to the hemoglobin concentration determining apparatus from an event input circuit 21 (FIG. 1), and displayed as an event on the display screen of the trend indicator 18. The event information may be oxygen inhalation, arrival at hospital, blood sampling for calibration, start of administering MB (methylene blue), and finish of administering MB or the like. The concentration ratios of oxyhemoglobin O2Hb, deoxyhemoglobin RHb and methemoglobin MetHb, which are processed in the Hb concentration ratio processing circuit 16, and the event information are transmitted to and stored in the storage circuit 19. Even after the power supply is interrupted or stopped, the data thus stored in the storage circuit 19 is still stored, and is displayed by the trend indicator 18.

As show in FIG. 6(A), trends of the concentrations of the hemoglobins may be displayed for both the functional and the fractional oxygen saturations (SpO2). The concentrations of the oxyhemoglobin O2Hb, deoxyhemoglobin RWb and methemoglobin MetHb may be displayed in terms of %, together with the event information (FIG. 6B). In the apparatus, the data that is stored in the storage circuit 19 may be sent to an external device, e.g., personal computer, through an external interface (FIG. 1).

The hemoglobin concentration determining apparatus shown in FIG. 1 includes calibration value input circuit 22 for inputting an in-blood light absorbing material concentration measured by the blood sampling. The data from the calibration value input circuit 22 is input to the Hb concentration ratio processing circuit 16. Based on the input values, the Hb concentration ratio processing circuit 16 performs calibration processes on the oxyhemoglobin O2Hb, deoxyhemoglobin RHb and methemoglobin MetHb. The calibration processing may be performed in the following way.

When a change of an attenuation by a pulsation of a living tissue, which is caused by a pulsation of blood is allowed for, a ratio $\Phi$ of the attenuations is expressed by (as described in JP-A-8-322822)

$$\Phi 12 = \Delta A1/\Delta A2 = [\sqrt{}$$
$$[(Eo1O2Hb + Er1RHb + Em$$
$$1MetHb)\{(Eo1O2Hb + Er$$
$$1RHb + Em1MetHb) + F\}] - Ex$$
$$]/[\sqrt{}[(Eo2O2Hb + Er$$
$$2RHb + Em2MetHb)\{(Eo2O2Hb + Er$$
$$2RHb + Em2MetHb) + F\}] - Ex] \qquad (5)$$

$$\Phi 13 = \Delta A1/\Delta A$$
$$3 = [\sqrt{}[(Eo1O2Hb + Er$$
$$1RHb + Em1MetHb)\{(Eo1O2Hb + Er$$
$$1RHb + Em1MetHb) + F\}] - Ex$$
$$]/[\sqrt{}[(Eo3O2Hb + Er$$
$$3RHb + Em3MetHb)\{(Eo3O2Hb + Er$$
$$3RHb + Em3MetHb) + F\}] - Ex] \qquad (5')$$

In the above equations, EX is a term indicating an attenuation caused by the pulsation of the pure tissue, and is unknown.

The unknown quantity EX may be determined by substituting the concentration values obtained by sampling blood for the above equations. Subsequently the simultaneous equations containing the thus determined unknown quantity EX are used, and highly accurate measurement results based on the pure tissue pulsation will be produced.

By use of a concentration of in-blood light-absorbing material determined through blood sampling, the attenuation ratios $\Phi$ stored in the storage circuit 19 before input of a calibration value or data on concentration ratios of respective hemoglobins can be re-processed, thus retroactively providing a highly accurate measurement result.

Further, when treatment is started, such as when administration of nitrogen monoxide (NO) or a vasodilator is started for a vasodilation therapy, when administration of a toponarcosis is started, or when anesthetic inhalation is started, each of the times called as a reference time, a tentative value (e.g., 0) is input to the calibration value input circuit as a calibration value for carboxyhemoglobin (CoHb) and/or methemoglobin (MetHb), instead of inputting a concentration value obtained by blood sampling as a calibration value. By doing this variation (primarily an increment due to administration) in the concentration of carboxyhemoglobin (CoHb) and/or methemoglobin (MetHb) can be determined after start of the treatment.

It has already been known that anesthetic inhalation using a drying agent causes carboxyhemoglobin to be generated in the body. Hence, it is useful to determine increased amount of carboxyhemoglobin generated in the body after start of the anesthetic inhalation.

Further even when an input circuit for inputting treatment start time (the time may precede initiation of a therapy) is provided, instead of a calibration value input circuit, variation in the concentration of carboxyhemoglobin (CoHb) and/or methemoglobin (MetHb) generated after start of the treatment can be measured.

Another calibration process will be described. The calibration process is applied for a calibration on an error caused by other light absorbing materials in blood, such as carboxyhemoglobin and bilirubin. A processing expression constructed while allowing for carboxyhemoglobin COHb is given by $$\Phi 12 = \Delta A1/\Delta A$$

$$2 = [\sqrt{[(Eo1O2Hb+Er}$$

$$1RHb+Ec1COHb+Em1MetHb)\{(Eo$$

$$1O2Hb+Er1RHb+Ec1COHb+Em$$

$$1MetHb)+F\}]-Ex]/[\sqrt{}$$

$$[(Eo2O2Hb+Er2RHb+Ec$$

$$2COHb+Em2MetHb)\{(Eo2O2Hb+Er$$

$$2RHb+Ec2COHb+Em2MetHb)$$

$$+F\}]-Ex] \quad (6)$$

$$\Phi 13 = \Delta A1/\Delta A3 = [\sqrt{}$$

$$[(Eo1O2Hb+Er1RHb+Ec$$

$$1COHb+Em1MetHb)\{(Eo1O2Hb+Er$$

$$1RHb+Ec1COHb+Em1MetHb)+F\}]$$

$$-Ex]/[\{\sqrt{[(Eo}$$

$$3O2Hb+Er3RHb+Ec3COHb+Em$$

$$3MetHb)\{(Eo3O2Hb+Er$$

$$3RHb+Ec3COHb+Em3MetHb)$$

$$+F\}]-Ex] \quad (6')$$

The unknown quantity EX may be processed by substituting measured O2Hb, RHb, MetHb, and COHb for the above equations. Further, the concentration ratios of the hemoglobins O2Hb, RHb and MetHb may be obtained by substituting the processed unknown quantity EX and the methemoglobin MetHb measured by the blood sampling method for the equations, and solving the simultaneous equations on the assumption that EX and COHb are constant. Incidentally, in an alternative processing, terms of bilirubin are incorporated into the above equations, and a bilirubin value measured by the blood sampling method is substituted for the equations. The same thing is valid for any of other in-blood light absorbing materials instead of bilirubin.

Figure 7:
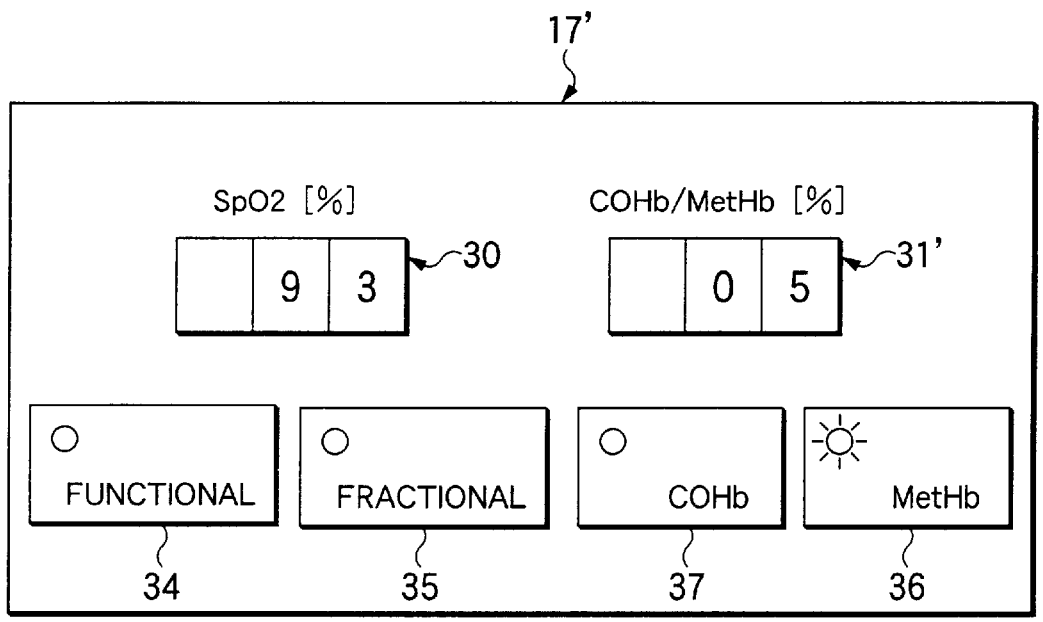
FIG. 7 is a descriptive view showing an example configuration of a hemoglobin Hb concentration indicator according to another embodiment of the hemoglobin concentration determining apparatus according to the present invention.

FIG. 7 shows another embodiment of the apparatus for determining concentrations of hemoglobins according to the present invention, showing an example configuration of an Hb concentration indicator 17' corresponding to the Rb concentration indicator 17 shown in FIG. 2. In more detail, the Hb concentration indicator 17' employed in the embodiment determines concentration of methemoglobin MetHb or carboxyhemoglobin COHb. In COHb/MetHb select Switch circuit 27 shown in FIG. 1, by selectively activating MetHb determination button 36 or COHb determination button 37, the equations for processing the concentration of methemoglobine MetHb described in connection with the Hb concentration ratio processing circuit 16 (see Equations 4, 4', 5 and 5) or the equations for processing the concentration of carboxyhemoglobin COHb are selectively applied, whereby the concentration of MetHb or COHb is processed as a percentage. The thus-processed concentration of MetHb or CoHb % can be displayed on COHb/MetHb concentration numerical value display section 31'.

In other respects, the apparatus is identical in configuration and operation with the previously-described apparatus shown in FIG. 2. Like elements are assigned like reference numerals, and their detailed explanations are omitted. A processing equation for determining carboxyhemoglobin COHb is as described in U.S. patent application Ser. No. 09/725865 proposed by the present inventor. In short, the processing equation can be achieved, by replacing all the coefficients relevant to methemoglobin MetHb in the equations for processing the concentration of methemoglobin MetHb (see Equations 4 and 5) with coefficients relevant to carboxyhemoglobin COHb.

The apparatus can also be provided with a risk level indication section which generates an alarm such as a sound or indicates a risk level such as that shown in FIGS. 3 and 4 when an attenuation ratio processed for the hemoglobin selected by either the MetHb determination button 36 or the COHb determination button 37 has exceeded the range of a predetermined threshold value.

Figure 8:
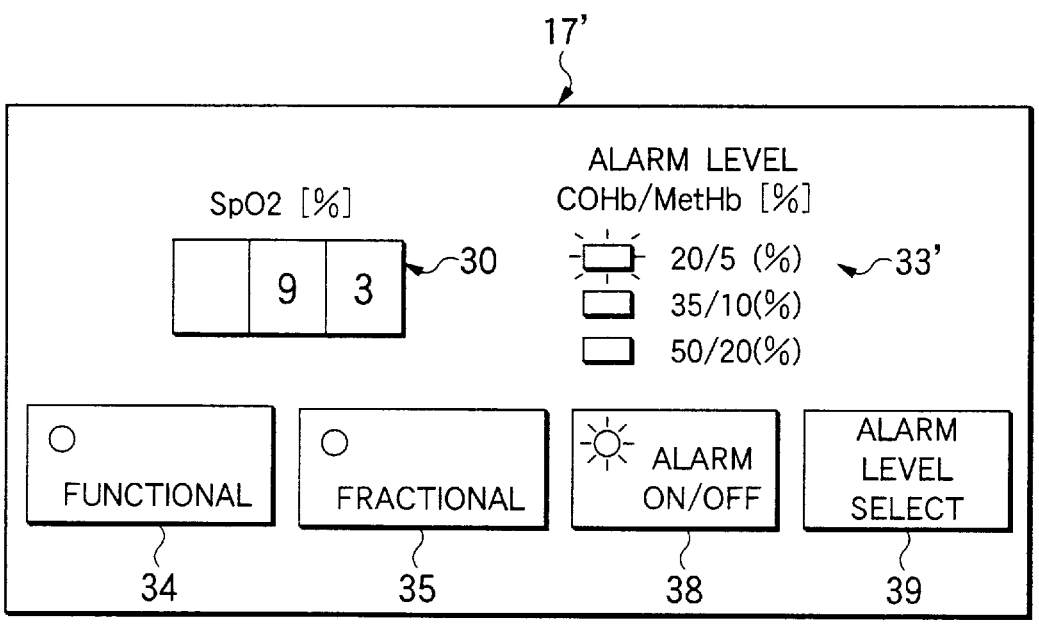
FIG. 8 is a descriptive view showing another example of configuration of the hemoglobin Hb concentration indicator shown in FIG. 7.

FIG. 8 shows another configuration example of the Hb concentration indicator 17' shown in FIG. 7. The indicator corresponds to the Hb concentration indicator 17 shown in FIG. 4. The Hb concentration indicator 17' is provided with an alarm activation/deactivation switch 38 for selectively activating/deactivating an abnormal hemoglobin detection function; and a risk level select switch 39 for selectively setting a risk level to be used for generating an alarm. In this case, after the alarm activation/deactivation switch 38 has been activated, a required alarm is generated when there has been detected a possibility of generation of concentrations of methemoglobin MetHb or carboxyhemoglobin COHb greater than a preset level. The preset level to be used for generating an alarm is expressed by combination of CoRb/MetHb. The requirement [$O_2$Hb=50%, COHb=50%] and the requirement [$O_2$Hb=80%, MetHb=20%] represent the same attenuation ratio. An alarm setting level is selectively determined as, for example, 50/20 (%), 35/10 (%), or 20/5 (%) (COBb/MetHb), by means of the risk level select switch 39. The thus-selected risk level can be displayed on the risk level display section 33' having readings provided thereon. In other respect, the apparatus is identical in configuration and operation with that shown in FIG. 4. Like elements are given like reference numerals, and their detailed explanations are omitted.

A calibration process employed for the case where methylene blue is administered to a methemoglobinemia patient will be described. As mentioned previously, the processing equation for determining the concentration of methemoglobin MetHb using three wavelengths is as expressed by Equations (2). Immediately before administration of methylene blue, a carbon monoxide oximeter performs measurement operation, thereby calibrating the pulse oximeter. In this case, the equations are the same as those expressed by Equations (6 and 6'). Provided that deoxyhemoglobin RHb, carboxyhemoglobin COHb, and the unknown EX remain unchanged during a medical treatment using methylene blue, the value used for calibration is substituted into the equations, thereby determining two variables: that is, oxyhemoglobin $O_2Hb$ and methemoglobin MetHb. When methylene blue is administered, the equations are expressed as follows:

$$\Phi 12 = \Delta A1/\Delta A2 = [\sqrt{}$$

$$[(Eo1O2Hb + Er1RHb + Ec$$

$$1COHb + Em1MetHb + Ed1Cd)\{(Eo$$

$$1O2Hb + Er1RHb + Ec1COHb + Em$$

$$1MetHb + Ed1Cd) + F\}]$$

$$-Ex]/[\sqrt{}[(Eo$$

$$2O2Hb + Er2RHb + Ec2COHb + Em$$

$$2MetHb + Ed2Cd)\{(Eo2O2Hb + Er$$

$$2RHb + Ec2COHb + Em2MetHb + Ed2Cd)$$

$$+F\}] - Ex] \tag{7}$$

$$\Phi 13 = \Delta A1/\Delta A3 =$$

$$[\sqrt{}[(Eo1O2Hb + Er$$

$$1RHb + Ec1COHb + Em1MetHb + Ed$$

$$1Cd)\{(Eo1O2Hb + Er1RHb + Ec$$

$$1COHb + Em1MetHb + Ed1Cd)$$

$$+F\}] - Ex]/[\sqrt{}[(Eo$$

$$3O2Hb + Er3RHb + Ec3COHb + Em$$

$$3MetHb + Ed3Cd)\{(Eo3O2Hb + Er$$

$$3RHb + Ec3COHb + Em3MetHb + Ed$$

$$3Cd) + F\}] - Ex] \tag{7'}$$

If the patient is known as not having inhaled carbon monoxide, there is no necessity for measurement by carbon nonoxide oximeter and also no necessity for calibrating the pulse oximeter. If a processing method which does not take into consideration the unknown EX is adopted, there may be employed a processing equation using EX=0 for Equations (6 and 6'). The same also applies to the subsequent equations.

In the equations, Edi represents an absorption coefficient of methylene blue; i=1 represents an optical wavelength $\lambda 1$; i=2 represents an optical wavelength $\lambda 2$; i=3 represents an optical wavelength $\lambda 3$; and Cd represents the concentration of methylene blue in blood. Provided that RHb, COHb, and EX remain unchanged, if the value used for calibration is substituted into the equations, thereby determining three variables; that is, $O_2Hb$, MetHb, and Cd. Since there are two processing equations, a ratio between the concentration of $O_2Hb$, that of MetHb, and that of Cd can be determined by solving the simultaneous equations. In other words, there can be determined a ratio of concentrations of $O_2Hb$ and those of MetHb. Thus, the therapeutic effect of a reduction in methemoglobin MetHb can be continuously monitored. In actual treatment of methemoglobinemia, the oxygen transport capability of blood remains in a low level. Normally, the patient is caused to inhale 100% oxygen $O_2$, and hence deoxyhemoglobin Rhb in arterial blood is close to 0, and carboxyhemoglobin COHb is rarely held in a concentrated state. For these reasons, the assumption that RHb and COHb assume a value of nearly 0 and remain unchanged is sufficiently practical. In connection with operation of an actual apparatus, the apparatus is provided with a switch indicating administration of methylene blue, In a subsequent process, calibration process can be performed according to processing equations having RHb and COHb as stationary constants by means of activating the switch.

While the preferred embodiment of the invention has specifically be described it should be understood that the present invention is not limited to the embodiment mentioned above, but may variously be modified, altered and changed within the spirits of the invention.

As is evident from the embodiments, an apparatus for determining concentrations of hemoglobins according to the present invention comprises:

a light source which emits at least light in a near-infrared wavelength region as a first wavelength, light in a red wavelength region as a second wavelength, and light in a red orange wavelength region as a third wavelength;

light-receiving means for receiving light that has originated from the light source and has passed through or has been reflected by a living tissue;

attenuation ratio processing means which processes an attenuation ratio $\Phi$ between the light rays of the wavelengths in accordance with a change in a received-light output signal in each wavelength output from the light-receiving means as a result of pulsation of blood; and concentration ratio comparison means which processes at least a proportion of the concentration of oxyhemoglobin and that of methemoglobin. Changes in transmitted light due to a change by methemoglobin MetHb can be detected at a good signal-to-noise ratio. Further, discrimination between methemoglobin MetHb and deoxyhemoglobin RHb is facilitated, thus enabling accurate measurement of methemoglobin MetHb.

In relation to the measuring apparatus according to the present invention, since measurement using two wavelengths is less susceptible to the influence of pulsation of a tissue than measurement using three wavelengths, the "MetHb determination button 36" is deactivated for a patient free of doubt about carbon monoxide poisoning, whereby an oxygen saturation ($SpO_2$) can be determined using two wavelengths according to a conventionally-practiced method. In contrast, for the case of a patient involving double about chemical poisoning, the "MetHb determination button 36" is activated, thereby enabling determination of concentrations of hemoglobins of various types including methemoglobin MetHb using three wavelengths, Even if an accurate concentration of methemoglobin is not displayed on a per-percentage basis, indication of presence/absence of methemoglobin or a risk level is very useful for a rescue member in determining whether to carry a patient to a hospital having a facility for hyperbaric oxygenation or methylene blue therapy or useful for a medical stuff to make a therapeutic plan. Further, using concentrations of light-absorbing materials in blood determined by blood sampling as calibration values enables more accurate determination of concentrations of hemoglobins.

According to the present invention, the most accurate method of determining the concentration of methemoglobin MetHb in blood is a blood sampling determination method using a carbon monoxide oximeter (CO-Oximeter). So long as the apparatus is calibrated through use of such a highly-reliable measurement value, the accuracy of a measurement value can be improved. A patient who suffers from acute chemical poisoning is usually subjected to oxygen inhalation and administration of methylene blue. Even at the time of such a treatment, a process of a reduction in the concentration of methemoglobin MetHb can be monitored with high reliability.

When the apparatus for determining concentrations of hemoglobins is used, the concentrations of three hemoglobins, i.e., Methemoglobin concentration, deoxyhemoglobin concentration and fractional oxygen saturation (oxyhemoglobin concentration), are displayed on the X-Y coordinates and hence one can visually grasp those concentrations at a time.

In the apparatus, a change of each hemoglobin concentration with time may be checked together with an event marker or the like concerning the treatment for the patient. The data obtained is very useful in deciding the course of treatment. Further, the effects of the treatment can visually be checked.

The apparatus according to the present invention can be constructed so as to be able to determine the concentration of a selected substance through use of selected processing equations for determination, by selecting determination of methemoglobin MetHb or determination of carboxyhemoglobin COHb. In this case, the apparatus can be constructed so as to be able to display presence of an abnormal hemoglobin, i.e., either methemoglobin MetHb or carboxyhemoglobin COHb. If an unconscious patient is found in a site where first aid is administered and the patient is found to have an abnormal hemoglobin, blood is immediately sampled from the patient to determine whether the abnormal hemoglobin is methemoglobin MetHb or carboxyhemoglobin COHb, thereby enabling administration of immediate and appropriate medical treatment. Further, during the course of medical treatment of methemoglobinemia using methylene blue, the apparatus according to the present invention enables appropriate measurement of the concentration of methemoglobin MetHb while obviating an influence of methylene blue.

The apparatus for determining concentrations of hemoglobins according to the present invention further comprises:

input means for entering a reference time; and concentration variation processing means for processing variation in the concentration of at least either carboxyhemoglobin or methemoglobin having arisen since the reference time entered by way of the input means.

By means of this configuration, a physician who performs medical treatment performs an input operation for causing the apparatus to recognize, e.g., when the treatment is initiated, as a reference time by way of the input means. There can be processed variation in the concentration of at least either carboxyhemoglobin or methemoglobin having arisen since the reference time input by way of the input means.

Moreover, the input means corresponds to calibration value input means; and the concentration variation processing means processes variation in a concentration having arisen since the reference time, by inputting a tentative value by way of the calibration value input means as a concentration of light-absorbing material in blood.

As a result, provided that time when a medical treatment has been initiated is taken as a reference time, there can be processed variation in the concentration of carboxyhemoglobin or methemoglobin having arisen since the reference time, by inputting a tentative value by way of the calibration value input means as a concentration of light-absorbing material in blood such as that of carboxyhemoglobin or methemoglobin.

What is claimed is:

1. An apparatus for determining concentrations of hemoglobins comprising:

a light source for emitting lights of at least three different wavelengths, a first wavelength in a near-infrared wavelength region, a second wavelength in a red wavelength region, and a third wavelength in a red orange wavelength region;

a light receiving means for receiving light emitted by the light source, transmitted through a living tissue or reflected by the living tissue;

attenuation ratio processing means for processing attenuation ratios between the wavelengths in accordance with variations of received-light output signals in each of the wavelengths output from the light receiving means, the variations are caused by a pulsation of blood; and concentration ratio processing means for processing concentration ratios of at least oxyhemoglobin and methemoglobin based on the output signals from the attenuation ratio processing means.

2. An apparatus for determining concentrations of hemoglobins according to claim 1, wherein the concentration ratio processing means is configured so as to process a proportion between an ever-changing concentration of oxyhemoglobin, an ever-changing concentration of methemoglobin, and an ever-changing concentration of methylene blue when medical treatment of methemoglobinemia is performed by administration of methylene blue into a living tissue, provided that at least a concentration of deoxyhemoglobin and that of carboxyhemoglobin remains unchanged.

3. An apparatus for determining concentrations of hemoglobins comprising:

a light source for emitting a plurality of lights of different wavelengths;

light receiving means for receiving light emitted by the light source, transmitted through a living tissue or reflected by the living tissue;

attenuation ratio processing means for processing attenuation ratios between the wavelengths in accordance with variations of received-light output signals in each of the wavelengths output from the light receiving means, the variations caused by a pulsation of blood;

concentration ratio processing means for processing concentration ratios of at least oxyhemoglobin, deoxyhemoglobin and methemoglobin based on the output signals from the attenuation ratio processing means; and oxygen saturation processing means for processing one of a functional oxygen saturation and a fractional oxygen saturation based on an output signals of the concentration ratio processing means.

4. An apparatus for determining concentrations of hemoglobins comprising:

a light source for emitting a plurality of lights of different wavelengths;

light receiving means for receiving light emitted by the light source, transmitted through a living tissue or reflected by a living tissue;

attenuation ratio processing means for processing attenuation ratios between the wavelengths in accordance with variations of received-light output signals in each of the wavelengths output from the light receiving means, the variations caused by a pulsation of blood;

concentration ratio processing means for processing concentration ratios of at least oxyhemoglobin and methemoglobin based on the output signals from the attenuation ratio processing means; and alarm display means for displaying an alarm in accordance with a level of a concentration ratio of methemoglobin obtained by the concentration ratio processing means.

5. An apparatus for determining concentrations of hemoglobins comprising:

a light source for emitting a plurality of lights of different wavelengths;

light receiving means for receiving light emitted by the light source, transmitted through a living tissue or reflected by the living tissue;

attenuation ratio processing means for processing attenuation ratios between the wavelengths in accordance with variations of received-light output signals in each of the wavelengths output from the light receiving means, the variations caused by a pulsation of blood;

concentration ratio processing means for processing concentration ratios of at least oxyhemoglobin and methemoglobin based on the output signals from the attenuation ratio processing means;

event input means for inputting information on the medical treatment or information on a patient as an event when the event occurs; and storage means for storing times when information is input and event information or input by the event input means, and the processing results output from the concentration ratio processing means.

6. An apparatus for determining concentrations of hemoglobins according to claim 5, further comprising:

display means for displaying the processing results in the form of a trend display together with the event information stored in the storage means at a corresponding time of the trend display.

7. An apparatus for determining concentrations of hemoglobins according to claim 5, further comprising:

an interface used for transmitting the event information, the times and the processing results, which are stored in the storage means, to an external device.

8. An apparatus for determining concentrations of hemoglobins comprising:

a light source for emitting a plurality of lights of different wavelengths;

light receiving means for receiving light emitted by the light source, transmitted through the living tissue or reflected by the living tissue;

calibration value input means for inputting a concentration value of at least one kind of light absorbing material in blood for calibration;

attenuation ratio processing means for processing attenuation ratios between the wavelengths in accordance with variations of received-light output signals in each of the wavelengths output from the light receiving means, the variations caused by a pulsation of blood; and concentration ratio processing means for processing concentration ratios of at least oxyhemoglobin and methemoglobin based on the output signals from the attenuation ratio processing means and the concentration of light-absorbing material input by way of the calibration value input means.

9. An apparatus for determining concentrations of hemoglobins comprising:

a light source for emitting a plurality of lights of different wavelengths;

light receiving means for receiving light emitted by the light source, transmitted through or reflected by a living tissue;

attenuation ratio processing means for processing attenuation ratios between the wavelengths in accordance with variations of received-light output signals in each of the wavelengths output from the light receiving means, which variations are caused by a pulsation of blood;

concentration ratio processing means for processing concentration ratios of at least oxyhemoglobin and methemoglobin based on the output signals from the attenuation ratio processing means; and select means for giving an instruction to process a concentration ratio of methemoglobin;

wherein when the select means does not give an instruction to process a concentration ratio of methemoglobin, the concentration ratio processing means processes at least a concentration ratio of oxyhemoglobin on the basis of variations of signals output from the light receiving means upon reception of lights of at least two different wavelengths that are emitted from the light source and transmitted through and reflected by a living tissue, and wherein when the select means gives an instruction to process a concentration ratio of methehemoglobin, the concentration ratio processing means processes at least concentration ratios of oxyhemoglobin and methemoglobin on the basis of variations of signals output from the light receiving means upon reception of lights of at least three different wavelengths that are emitted from the light source and transmitted through and reflected by a living tissue.

10. An apparatus for determining concentrations of hemoglobins comprising:

a light source for emitting a plurality of lights of different wavelengths;

light receiving means for receiving light emitted by the light source, transmitted through a living tissue or reflected by the living tissue;

attenuation ratio processing means for processing attenuation ratios between the wavelengths in accordance with variations of received-light output signals in each of the wavelengths output from the light receiving means, the variations caused by a pulsation of blood;

concentration ratio processing means for processing concentration ratios of at least oxyhemoglobin deoxyhemoglobin and methemoglobin based on the output signals from the attenuation ratio processing means; and display means for displaying measured values of oxyhemoglobin, deoxyhemoglobin and methemoglobin on the X-Y coordinates.

11. An apparatus for determining concentrations of hemoglobins as claimed in claim 3, wherein the light source for emitting lights are at least three different wavelengths, a first wavelength in a near-infrared region, a second wavelength in a red region, and a third wavelength in a red orange region.

12. An apparatus for determining concentrations of hemoglobins comprising:
- a light source for emitting lights of at least three different wavelengths, a first wavelength in a near infrared region, a second wavelength in a red region, and a third wavelength in a red orange region;
- light receiving means for receiving light emitted by the light source, transmitted through a living tissue or reflected by the living tissue;
- attenuation ratio processing means for processing attenuation ratios between the wavelengths in accordance with variations of received-light output signals in each of the wavelengths output from the light receiving means, the variations are caused by a pulsation of blood; and
- concentration ratio processing means for processing concentration ratios of at least oxyhemoglobin, carboxyhemoglobin and methemoglobin based on the output signals from the attenuation ratio processing means; and
- switch means for causing the concentration ratio processing means to selectively process a concentration ratio of carboxyhemoglobin to that of methemoglobin.

13. An apparatus for determining concentrations of hemoglobins as claimed in claim 12, wherein a predetermined threshold is set for an attenuation ratio to be processed by the attenuation ratio processing means, and further comprising;
- display means for displaying an alarm when an attenuation ratio processed for the hemoglobin to which the switch means has been switched has exceeded the threshold value.

14. An apparatus for determining concentrations of hemoglobins comprising:
- a light source for emitting lights of at least three different wavelengths, a first wavelength in a near-infrared region, a second wavelength in a red region, and a third wavelength in a red orange region;
- light receiving means for receiving light emitted by the light source, transmitted through a living tissue or reflected by the living tissue;
- attenuation ratio processing means for processing attenuation ratios associated with concentrations of carboxyhemoglobin and methemoglobin in accordance with variations of received-light output signals in each of the wavelengths output from the light receiving means, the variations are caused by a pulsation of blood; and
- display means for displaying an alarm when at least one of a processed attenuation ratio of carboxyhemoglobin and a processed attenuation ratio of methemoglobin has exceeded a range of a predetermined threshold value, the threshold value being set for an attenuation ratio of carboxyhemoglobin and an attenuation ratio of methemoglobin which are to be processed by the attenuation ratio processing means.

15. An apparatus for determining concentrations of hemoglobins according to claim 1, wherein the light source for emitting lights of at least three different wavelengths, a first wavelength selected from a near-infrared wavelength region of 790 to 1000 nm, a second wavelength from a red wavelength region of 640 to 675 nm, and a third wavelength from a red orange wavelength region of 590 to 660 nm.

16. An apparatus for determining concentrations of hemoglobins according to claim 15, wherein the third wavelength in a red orange wavelength region is 621 nm.

17. An apparatus for determining concentrations of hemoglobins comprising:
- a light source for emitting a plurality of lights of different wavelengths;
- light receiving means for receiving light emitted by the light source, transmitted through a living tissue or reflected by a living tissue;
- calibration value input means for inputting a concentration value of at least one kind of light absorbing material in blood for calibration;
- attenuation ratio processing means for processing attenuation ratios between the wavelengths in accordance with variations of received-light output signals in each of the wavelengths output from the light receiving means, the variations caused by a pulsation of blood;
- storage means for storing data concerning the attenuation ratios; and
- concentration ratio processing means for retroactively re-process of at least a concentration ratio of oxyhemoglobin and a concentration ratio of methemoglobin, through use of the data stored in the storage means and the concentrations of light-absorbing materials in blood entered by way of the calibration value input means.

18. An apparatus for determining concentrations of hemoglobins, comprising:
- a light source for emitting a plurality of lights of different wavelengths;
- light receiving means for receiving a plurality of light emitted by the light source, transmitted through a living tissue or reflected by a living tissue;
- input means for entering a reference time;
- attenuation ratio processing means for processing attenuation ratios between the wavelengths in accordance with variations of received-light output signals in each of the wavelengths output from the light receiving means, the variations caused by a pulsation of blood; and
- concentration variation processing means for processing variation in the concentration of at least one of carboxyhemoglobin and methemoglobin having arisen since the reference time entered by way of the input means.

19. The apparatus for determining concentrations of hemoglobins according to claim 18, wherein the input means corresponds to calibration value input means, and the concentration variation processing means processes variation in the concentration since the reference time by inputting a tentative value by way of the calibration value input means as a concentration of light-absorbing material in blood.

* * * * *